US011596773B2

(12) United States Patent
Sorensen et al.

(10) Patent No.: US 11,596,773 B2
(45) Date of Patent: Mar. 7, 2023

(54) METHOD AND APPARATUS FOR ANCHORING A CATHETER LINE TO THE TISSUE OF A PATIENT FOR PAIN PUMP DRUG DELIVERY

(71) Applicant: Anchor Innovation Medical, Inc., Basking Ridge, NJ (US)

(72) Inventors: Peter Sorensen, Salem, MA (US); Daniel Morgan, Salem, MA (US); Christopher Runnells, Madison, NJ (US); Lee Griffith, Basking Ridge, NJ (US)

(73) Assignee: Anchor Innovation Medical, Inc., Basking Ridge, NJ (US)

( * ) Notice: Subject to any disclaimer, the term of this patent is extended or adjusted under 35 U.S.C. 154(b) by 1018 days.

(21) Appl. No.: 16/059,929

(22) Filed: Aug. 9, 2018

(65) Prior Publication Data

US 2019/0046773 A1    Feb. 14, 2019

Related U.S. Application Data

(60) Provisional application No. 62/542,912, filed on Aug. 9, 2017.

(51) Int. Cl.
*A61M 25/04* (2006.01)
*A61M 25/02* (2006.01)
(Continued)

(52) U.S. Cl.
CPC ........ *A61M 25/04* (2013.01); *A61M 5/14276* (2013.01); *A61M 25/0133* (2013.01);
(Continued)

(58) Field of Classification Search
CPC .......... A61M 25/02; A61M 2025/0286; A61M 2025/0233; A61M 2025/0293;
(Continued)

(56) References Cited

U.S. PATENT DOCUMENTS 4,553,961 A * 11/1985 Pohndorf ............... A61B 17/04
604/175
5,152,298 A * 10/1992 Kreyenhagen ..... A61B 17/0401
604/175
(Continued)

FOREIGN PATENT DOCUMENTS

EP           1475123 A1 * 11/2004 ............ A61M 25/02
WO     WO-2005030316 A1 * 4/2005 .......... F16L 37/0841

OTHER PUBLICATIONS

Boston Scientific, FixateTM Suturing Device Directions for Use, 2013.
Boston Scientific, Percutanous Leads: Directions for Use, 2017.

*Primary Examiner* — Nilay J Shah
(74) *Attorney, Agent, or Firm* — Pandiscio & Pandiscio

(57) ABSTRACT

The present invention includes the provision and use of a novel method and apparatus for anchoring a catheter line to the tissue of a patient (e.g., the internal fascia of a patient) for pain pump drug delivery. In one preferred form of the invention, the invention includes the provision and use of a catheter line fixation device including a housing and a collet assembly. The catheter line fixation device is intended to be adjustably secured to a catheter line, and the catheter line fixation device is intended to be secured to the tissue of a patient (e.g., the internal fascia of a patient), so as to secure the catheter line to the tissue of the patient.

18 Claims, 16 Drawing Sheets

(51) Int. Cl.
*A61M 5/142* (2006.01)
*A61M 25/01* (2006.01)
*A61M 31/00* (2006.01)
*A61M 25/06* (2006.01)
*A61M 25/00* (2006.01)

(52) U.S. Cl.
CPC .......... *A61M 25/02* (2013.01); *A61M 31/002* (2013.01); *A61M 25/06* (2013.01); *A61M 2025/0007* (2013.01); *A61M 2025/0213* (2013.01); *A61M 2025/0286* (2013.01); *A61M 2025/0293* (2013.01)

(58) Field of Classification Search
CPC ...... A61M 2025/0213; A61M 5/14276; A61N 2001/0582; A61N 1/057; A61N 1/0558; A61N 1/059; A61N 1/37518

See application file for complete search history.

(56) References Cited

U.S. PATENT DOCUMENTS

| | | | |
|---|---|---|---|
| 5,476,493 A * | 12/1995 | Muff | A61N 1/057 604/175 |
| 7,184,841 B1 * | 2/2007 | Bodner | A61N 1/057 607/122 |
| 8,958,891 B2 * | 2/2015 | Kane | A61N 1/0558 607/126 |
| 9,242,074 B2 | 1/2016 | Olson | |
| 2005/0137664 A1 * | 6/2005 | Sommer | A61N 1/057 607/115 |
| 2006/0173520 A1 * | 8/2006 | Olson | A61M 25/02 607/115 |
| 2006/0264803 A1 * | 11/2006 | Lui | A61N 1/056 604/19 |
| 2008/0228251 A1 * | 9/2008 | Hill | A61N 1/057 607/126 |
| 2009/0125059 A1 * | 5/2009 | Verzal | A61N 1/057 606/232 |
| 2011/0224764 A1 | 9/2011 | Kulle | |
| 2012/0197367 A1 * | 8/2012 | Olson | A61N 1/057 607/116 |
| 2014/0323972 A1 | 10/2014 | Daglow | |
| 2017/0087351 A1 * | 3/2017 | Olson | A61N 1/05 |

* cited by examiner

METHOD AND APPARATUS FOR ANCHORING A CATHETER LINE TO THE TISSUE OF A PATIENT FOR PAIN PUMP DRUG DELIVERY

REFERENCE TO PRIOR PATENT APPLICATION

This patent application claims benefit of prior U.S. Provisional Patent Application Ser. No. 62/542,912, filed Aug. 9, 2017 by Anchor Innovation Medical, Inc. and Peter Sorensen et al. for METHOD AND APPARATUS FOR ANCHORING A CATHETER LINE TO INTERNAL TISSUE OF A PATIENT FOR PAIN PUMP DRUG DELIVERY, which patent application is hereby incorporated herein by reference.

FIELD OF THE INVENTION

This invention relates to pain pumps in general, and more particularly to methods and apparatus for anchoring a catheter line to the tissue of a patient for pain pump drug delivery.

BACKGROUND OF THE INVENTION

In pain pump drug delivery, a pain pump system is used to deliver medication to a selected area of the body of a patient so as to provide pain relief to the patient.

In one significant application of pain pump drug delivery, sometimes referred to as "intrathecal drug delivery", a pain pump system is used to deliver medication to the subarachnoid space in the spinal column of a patient, whereby to provide pain relief to the patient. See, for example, FIGS. 1 and 2, which show a pain pump system 5 for delivering medication to the spinal column of a patient. Pain pump system 5 generally comprises a spinal needle 10, a pain pump 15 (which includes a reservoir of medication) and a catheter line 20. Spinal needle 10 is positioned in the spinal column of a patient so that the distal tip of the spinal needle is disposed in the subarachnoid space which is to be treated, pain pump 15 is disposed within the torso of the patient, and catheter line 20 connects pain pump 15 to spinal needle 10 so that the pain pump can pump medication through the catheter line to provide pain relief to the patient.

In practice, catheter line 20 is sutured to the tissue of the patient (e.g., the internal fascia of the patient) so as to stabilize the catheter line within the body of the patient.

Unfortunately, the current practice of using sutures to hold the catheter line to the tissue of the patient (e.g., the internal fascia of the patient) is not completely satisfactory.

By way of example but not limitation, where the catheter line is a simple tube, the sutures may allow unintended movement (e.g., sliding) of the catheter line to occur, which could displace the spinal needle from its position within the spinal column of the patient. In addition, the direct contact of the sutures with the catheter line could lead to occlusion or kinking of the catheter line if the sutures were to be overtightened, which could affect proper dosing of the medication. Furthermore, the direct contact of the sutures with the catheter line may damage the catheter line, e.g., by abrasion, which could affect the structural integrity of the catheter line and, if such abrasion penetrates through to the inner lumen of the catheter line, could affect proper dosing of the medication.

By way of further example but not limitation, where the catheter line comprises a suture mount (e.g., an eyelet) disposed on the outer wall of the catheter line, the suture mount (e.g., an eyelet) is fixed in position along the length of the catheter line, and that position may not lie adjacent to the specific tissue of the patient (e.g., the internal fascia of the patient) to which the catheter line should be anchored. In other words, the suture mount (e.g., an eyelet) may not be ideally positioned relative to the tissue to which the catheter line is to be anchored. As a result, anchoring of the catheter line may be problematic.

Therefore, a primary object of the present invention is to provide an improved method and apparatus for anchoring a catheter line to the tissue of a patient (e.g., the internal fascia of a patient) for pain pump drug delivery.

SUMMARY OF THE INVENTION

The present invention comprises the provision and use of a novel method and apparatus for anchoring a catheter line to the tissue of a patient (e.g., the internal fascia of a patient) for pain pump drug delivery. In one preferred form of the invention, the invention comprises the provision and use of a catheter line fixation device. The catheter line fixation device is intended to be adjustably secured to a catheter line, and the catheter line fixation device is intended to be secured to the tissue of a patient (e.g., the internal fascia of the patient), so as to secure the catheter line to the tissue of the patient (e.g., the internal fascia of the patient).

In one form of the invention, there is provided apparatus for releasably securing an elongated component to tissue, said apparatus comprising:
a housing comprising:
a distal end portion terminating in a distal end surface, a proximal end portion terminating in a proximal end surface, and an intermediate portion disposed between said distal end portion and said proximal end portion; and
a passageway extending through said housing from said distal end surface to said proximal end surface, said passageway comprising a distal end section, a proximal end section, and an intermediate section disposed between said distal end section and said proximal end section;
wherein at least a portion of said housing is formed out of an elastomeric material so that said housing may be selectively longitudinally stretched so as to transform from a longitudinally-relaxed condition to a longitudinally-stretched condition; and
a collet assembly for disposition in said passageway of said housing, said collet assembly comprising:
a radially-compressible body comprising a tapered distal end region terminating in a distal end surface, a tapered proximal end region terminating in a proximal end surface, and a tubular intermediate region disposed between said tapered distal end region and said tapered proximal end region; and
a bore extending between said distal end surface of said body and said proximal end surface of said body, said bore being sized larger than the elongated component when said body is in a radially-uncompressed condition;
wherein said tapered distal end region of said body of said collet assembly is received in said distal end section of said passageway of said housing, and said tapered proximal end region of said body of said collet assembly is received in said proximal end section of said passageway of said housing;
wherein, when said housing is in its longitudinally-relaxed condition, said distal end section of said passageway of said housing engages said tapered distal end region of said body of said collet assembly, and said proximal end section of said passageway of said housing engages said tapered proximal end region of said body of said collet assembly, so as to radially compress said body of said collet assembly into a radially-compressed condition wherein said bore is sized smaller than the elongated component; and wherein, when said housing is in its longitudinally-stretched condition, said distal end section of said passageway of said housing disengages from said tapered distal end region of said body of said collet assembly, and said proximal end section of said passageway of said housing disengages from said tapered proximal end region of said body of said collet assembly, so as to no longer radially compress said body of said collet assembly.

In another form of the invention, there is provided a method for securing an elongated component to tissue, said method comprising:

providing apparatus for releasably securing an elongated component to tissue, said apparatus comprising:
a housing comprising:
a distal end portion terminating in a distal end surface, a proximal end portion terminating in a proximal end surface, and an intermediate portion disposed between said distal end portion and said proximal end portion; and
a passageway extending through said housing from said distal end surface to said proximal end surface, said passageway comprising a distal end section, a proximal end section, and an intermediate section disposed between said distal end section and said proximal end section;
wherein at least a portion of said housing is formed out of an elastomeric material so that said housing may be selectively longitudinally stretched so as to transform from a longitudinally-relaxed condition to a longitudinally-stretched condition; and
a collet assembly for disposition in said passageway of said housing, said collet assembly comprising:
a radially-compressible body comprising a tapered distal end region terminating in a distal end surface, a tapered proximal end region terminating in a proximal end surface, and a tubular intermediate region disposed between said tapered distal end region and said tapered proximal end region; and
a bore extending between said distal end surface of said body and said proximal end surface of said body, said bore being sized larger than the elongated component when said body is in a radially-uncompressed condition;
wherein said tapered distal end region of said body of said collet assembly is received in said distal end section of said passageway of said housing, and said tapered proximal end region of said body of said collet assembly is received in said proximal end section of said passageway of said housing;
wherein, when said housing is in its longitudinally-relaxed condition, said distal end section of said passageway of said housing engages said tapered distal end region of said body of said collet assembly, and said proximal end section of said passageway of said housing engages said tapered proximal end region of said body of said collet assembly, so as to radially compress said body of said collet assembly into a radially-compressed condition wherein said bore is sized smaller than the elongated component; and
wherein, when said housing is in its longitudinally-stretched condition, said distal end section of said passageway of said housing disengages from said tapered distal end region of said body of said collet assembly, and said proximal end section of said passageway of said housing disengages from said tapered proximal end region of said body of said collet assembly, so as to no longer radially compress said body of said collet assembly;

applying a longitudinally-stretching force to said housing so as to transform said housing from a longitudinally-relaxed condition to a longitudinally-stretched condition, whereby to transform said body of said collet assembly from its radially-compressed condition to its radially-uncompressed condition;

passing the elongated component through said passageway of said housing and said bore of said collet assembly;

removing the longitudinally-stretching force from said housing so as to transform said housing from a longitudinally-stretched condition to a longitudinally-relaxed condition, whereby to transform said body of said collet assembly from its radially-uncompressed condition to its radially-compressed condition; and securing said housing to tissue.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
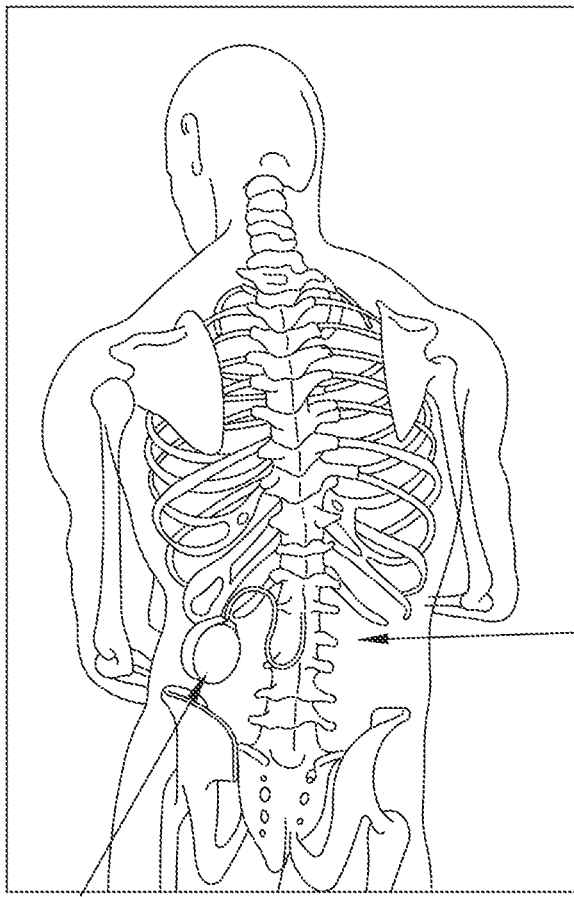
FIGS. 1 and 2 are schematic views showing a pain pump system disposed in the body of a patient.
Figure 2:
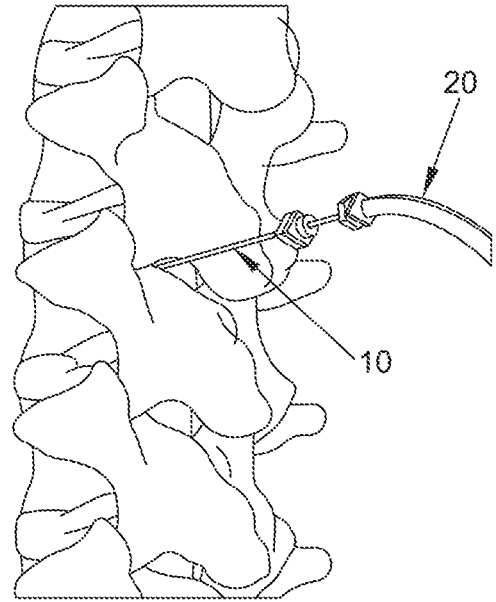
Figure 3:
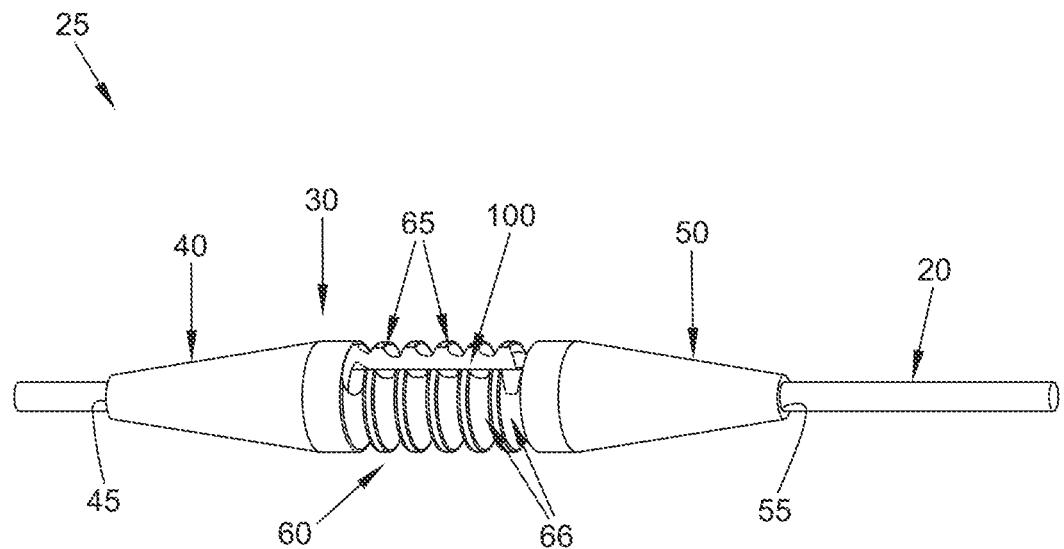
FIGS. 3-6 are schematic views showing a novel catheter line fixation device formed in accordance with the present invention.
Figure 4:
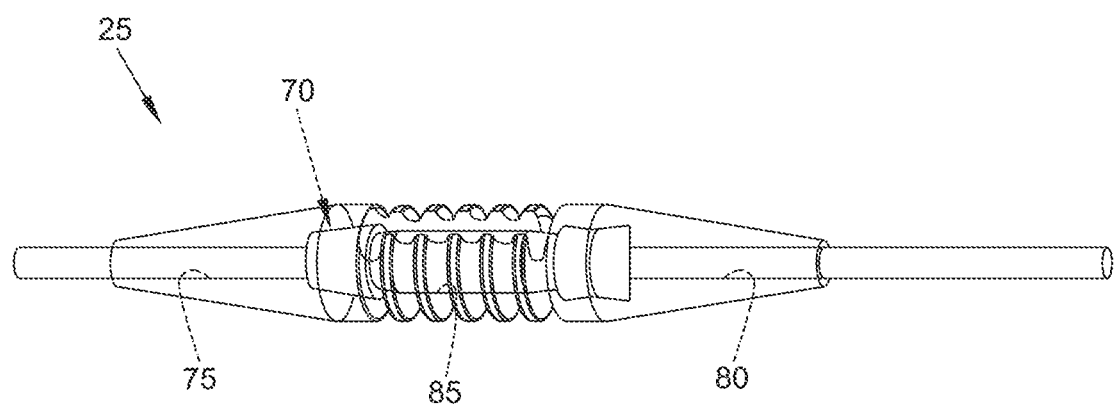
Figure 5:
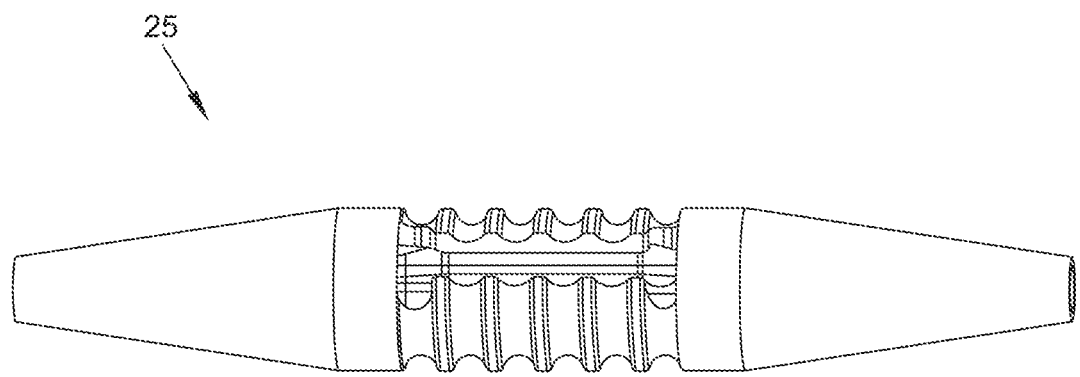
Figure 6:
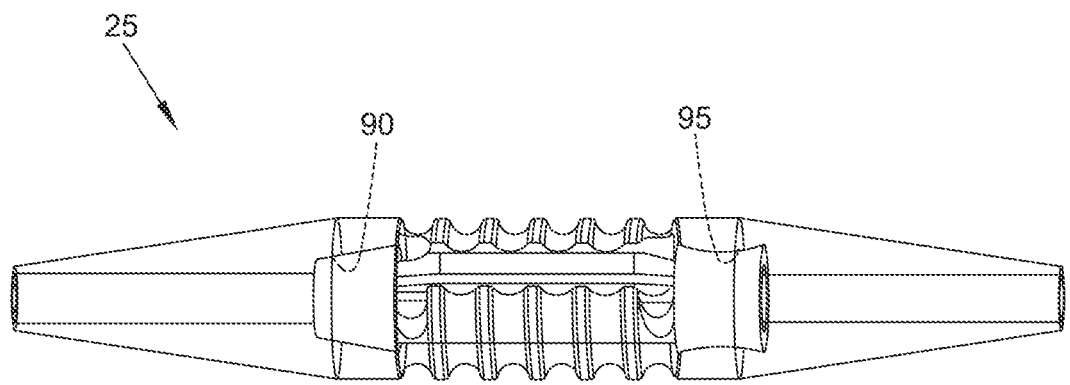
Figure 7:
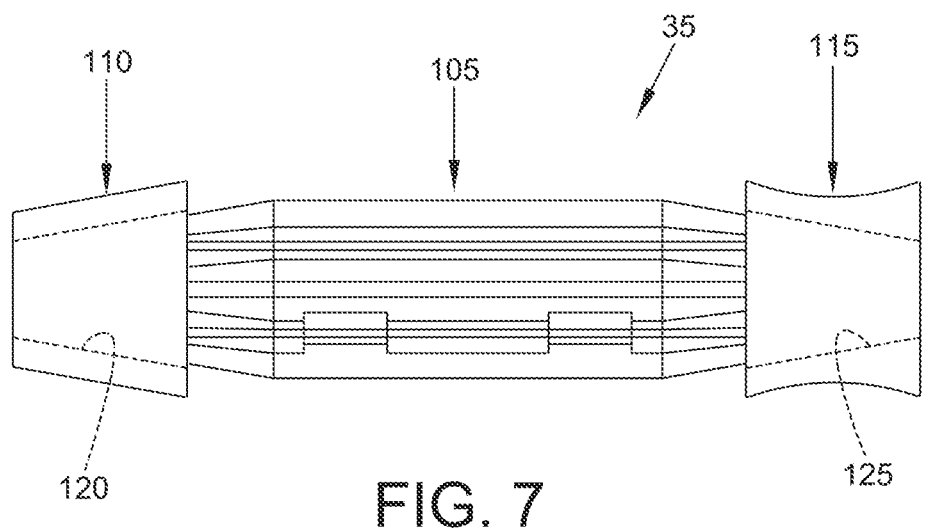
FIGS. 7-9 are schematic views showing further details of the collet assembly of the novel catheter line fixation device of FIGS. 3-6.
Figure 8:
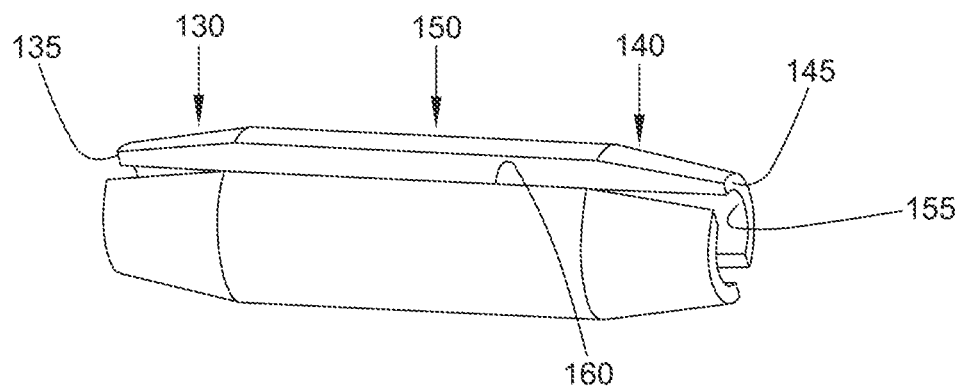
Figure 9:
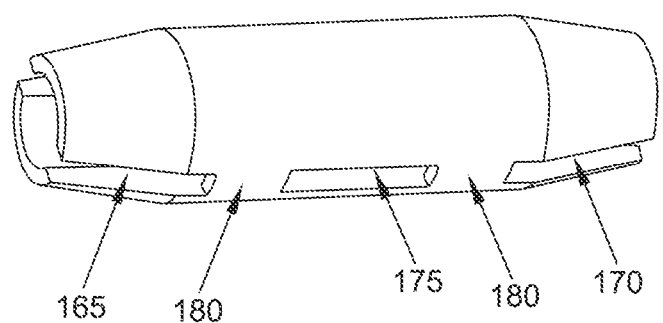

The present invention comprises the provision and use of a novel method and apparatus for anchoring a catheter line to the tissue of a patient (e.g., the internal fascia of a patient) for pain pump drug delivery. In one preferred form of the invention, the invention comprises the provision and use of a catheter line fixation device. The catheter line fixation device is intended to be adjustably secured to a catheter line, and the catheter line fixation device is intended to be secured to the tissue of a patient (e.g., the internal fascia of a patient), so as to secure the catheter line to the tissue of the patient (e.g., the internal fascia of the patient).

The Novel Catheter Line Fixation Device

More particularly, and looking now at FIGS. 3-9, there is shown a novel catheter line fixation device 25 formed in accordance with the present invention. Catheter line fixation device 25 generally comprises a housing 30 and a collet assembly 35. As will hereinafter be discussed, collet assembly 35 is disposed within housing 30 and serves to adjustably secure housing 30 of catheter line fixation device 25 to catheter line 20.

Housing 30 generally comprises a distal end portion 40 terminating in a distal end surface 45, a proximal end portion 50 terminating in a proximal end surface 55, and an intermediate portion 60 disposed between distal end portion 40 and proximal end portion 50.

In one preferred form of the invention, distal end portion 40 and proximal end portion 50 are tapered.

And in one preferred form of the invention, intermediate portion 60 comprises ribs 65 for receiving suture for securing catheter line fixation device 25 to the tissue of a patient (e.g., the internal fascia of a patient). More particularly, the troughs 66 disposed between the ribs 65 serve as seats for receiving the suture which secures catheter line fixation device 25 to the tissue of a patient.

Preferably the entire housing 30 is formed out of elastomeric material. Alternatively, intermediate portion 60 of housing 30 is formed out of elastomeric material and distal end portion 40 of housing 30, and proximal end portion 50 of housing 30, are formed out of non-elastomeric material(s).

A passageway 70 extends between distal end surface 45 and proximal end surface 55. More particularly, passageway 70 comprises a distal end section 75, a proximal end section 80 and an intermediate section 85. Passageway 70 also comprises a distal tapered section 90 which is located between distal end section 75 and intermediate section 85, and a proximal hourglass-shaped section 95 which is located between proximal end section 80 and intermediate section 85. Thus, proceeding distal to proximal, passageway 70 comprises the aforementioned distal end section 75, distal tapered section 90, intermediate section 85, proximal hourglass-shaped section 95 and proximal section 80. Distal end section 75 and proximal end section 80 are both sized so as to be just slightly larger than the outer diameter of catheter line 20, such that catheter line 20 can slide through distal end section 75 and proximal end section 80 (see below).

In a preferred form of the invention, an opening 100 is formed in intermediate section 85. Opening 100 communicates with intermediate section 85 of passageway 70.

Collet assembly 35 generally comprises a body 105, a tapered distal collet collar 110 and an hourglass-shaped proximal collet collar 115. Tapered distal collet collar 110 comprises a tapered opening 120, and hourglass-shaped collet collar 115 comprises a tapered opening 125. Tapered distal collet collar 110 is sized so as to be received within, and be secured to, distal tapered section 90 of passageway 70, and hourglass-shaped proximal collet collar 115 is sized so as to be received within, and be secured to, proximal hourglass-shaped section 95 of passageway 70.

In one form of the invention, tapered distal collet collar 110 is molded into distal tapered section 90 of passageway 70, and hourglass-shaped proximal collet collar 115 is molded into proximal hourglass-shaped section 95 of passageway 70. Note that tapered distal collet collar 110 and/or hourglass-shaped proximal collet collar 115 may be formed out of a material which is harder and/or less elastic than the material out of which housing 30 is formed.

Body 105 of collet assembly 35 comprises a tapered distal end region 130 terminating in a distal end surface 135, a tapered proximal end region 140 terminating in a proximal end surface 145, and a tubular intermediate region 150 extending between tapered distal end region 130 and tapered proximal end region 140. Tapered distal end region 130 of body 105 is slidably received within tapered opening 120 of tapered distal collet collar 110, and tapered proximal end region 140 of body 105 is slidably received within tapered opening 125 of hourglass-shaped proximal collet collar 115. A bore 155 extends through body 105, from distal end surface 135 to proximal end surface 145. Bore 155 is sized so as to be slightly smaller than the outer diameter of catheter line 20 when body 105 is in an unbiased condition (see below).

A slot 160 is formed in tapered distal end region 130, tubular intermediate region 150 and tapered proximal end region 140. Slot 160 communicates with bore 155.

A distal opening 165 is formed in tapered distal end region 130 and tubular intermediate region 140, a proximal opening 170 is formed in tapered proximal end region 140 and tubular intermediate region 150, and an intermediate opening 175 is formed in tubular intermediate region 150. Distal opening 165, intermediate opening 175 and proximal opening 170 are aligned with one another, and are diametrically opposed from slot 160. Distal opening 165, intermediate opening 175 and proximal opening 170 together define a pair of hinges 180.

At least hinges 180, and preferably the entire body 105 of collet assembly 35, comprise an elastomeric material, such that body 105 of collet assembly 35 can open and close about slot 160 on flexible hinges 180.

Collet assembly 35 is mounted within housing 30 so that (i) tapered distal collet collar 110 of collet assembly 35 is received within, and is secured to, distal tapered section 90 of passageway 70, (ii) hourglass-shaped proximal collet collar 115 of collet assembly 35 is received within, and is secured to, proximal hourglass-shaped section 95 of passageway 70, and (iii) body 105 of collet assembly 35 is disposed within intermediate section 85 of passageway 70.

As a result of this construction, when distal end portion 40 of housing 30 and proximal end portion 50 of housing 30 are forced apart, tapered distal collet collar 110 of collet assembly 35 and hourglass-shaped proximal collet collar 115 of collet assembly 35 are also forced apart (i.e., by virtue of the fact that tapered distal collet collar 110 is received within, and is secured to, distal tapered section 90 of passageway 70, and by virtue of the fact that hourglass-shaped proximal collet collar 115 is received within, and is secured to, proximal hourglass-shaped section 95 of passageway 70), whereby to move tapered distal collet collar 110 away from tapered distal end region 130 of body 105 and whereby to move hourglass-shaped proximal collet collar 115 away from tapered proximal end region 140 of body 105, so as to allow body 105 of collet assembly 35 to assume an unbiased condition and open on its hinges 180. In other words, when the two ends of housing 30 are stretched longitudinally apart, body 105 of collet assembly 35 is radially uncompressed.

Conversely, when the stretching force applied to distal end portion 40 of housing 30 and proximal end portion 50 of housing 30 is relaxed, and distal end portion 40 of housing 30 and proximal end portion 50 of housing 30 are allowed to return back towards one another (i.e., due to the elastomeric nature of intermediate portion 60 of housing 30), tapered distal collet collar 110 of collet assembly 35 and hourglass-shaped proximal collet collar 115 of collet assembly 35 also return back towards one another (i.e., by virtue of the fact that tapered distal collet collar 110 is received within, and is secured to, distal tapered section 90 of passageway 70, and by virtue of the fact that hourglass-shaped proximal collet collar 115 is received within, and is secured to, proximal hourglass-shaped section 95 of passageway 70), whereby to force tapered distal collet collar 110 against tapered distal end region 130 of body 105 and whereby to force hourglass-shaped proximal collet collar 115 against tapered proximal end region 140 of body 105, so as to cause body 105 of collet assembly 35 to assume a biased condition and close on its hinges 180. In other words, when the two ends of housing 30 are no longer stretched longitudinally apart, body 105 of collet assembly 35 is radially compressed.

Note that inasmuch as housing 30 (or at least intermediate portion 60 of housing 30) is elastomeric, tapered distal collet collar 110 of collet assembly 35 and hourglass-shaped proximal collet collar 115 of collet assembly 35 are normally biased together, whereby to close body 105 of collet assembly 35 on its hinges 180. Note also that when body 105 of collet assembly 35 is closed on its hinges 180, bore 155 of body 105 has a diameter smaller than the outer diameter of catheter line 20.

Thus, when distal end portion 40 of housing 30 and proximal end portion 50 of housing 30 are forced apart, body 105 of collet assembly 35 is able to open on its hinges, such that a catheter line 20 can be passed through bore 155 of body 105 and hence through passageway 70 of housing 30.

Conversely, when the stretching force applied to distal end portion 40 of housing 30 and proximal end portion 50 of housing 30 is thereafter released, body 105 of collet assembly 35 closes back down on its hinges 180, such that body 105 of collet assembly 35 securely grips a catheter line 20 which has been previously passed through bore 155 of body 105 and passageway 70 of housing 30.

Use of the Novel Catheter Line Fixation Device

In use:
(i) a spinal needle 10 is placed at the location in the spinal cord which is to receive the medication;
(ii) the distal end of catheter line 20 is positioned adjacent to spinal needle 10;
(iii) catheter line fixation device 25 is longitudinally stretched so that body 105 of collet assembly 35 is radially uncompressed, so that bore 155 of body 105 is larger than catheter line 20;
(iv) while catheter line fixation device 25 remains longitudinally stretched, the catheter line fixation device is loaded onto catheter line 20 and advanced to a position adjacent to where catheter line 20 is to be anchored to the tissue of the patient (e.g., the internal fascia of the patient);
(v) when catheter line 20 is located adjacent to where catheter line 20 is to be anchored to the tissue of the patient, the stretching force applied to catheter line fixation device 25 is released so that body 105 of collet assembly 35 is radially compressed, so that bore 155 of body 105 is smaller than catheter line 20, whereby to clamp catheter line fixation device 25 to catheter line 20;
(vi) any final adjustments are made to the position of catheter line fixation device 25 on catheter line 20 (i.e., by longitudinally stretching catheter line fixation device 25 so as to "unlock" catheter line fixation device 25 from catheter line 20, sliding catheter line fixation device 25 as desired along catheter line 20, and then releasing the stretching force on catheter line fixation device 25 so that catheter line fixation device 25 clamps once again to catheter line 20); and
(vii) sutures are used to secure catheter line fixation device 25 (and hence catheter line 20) to the tissue of the patient (e.g., the internal fascia of the patient).

Figure 10:
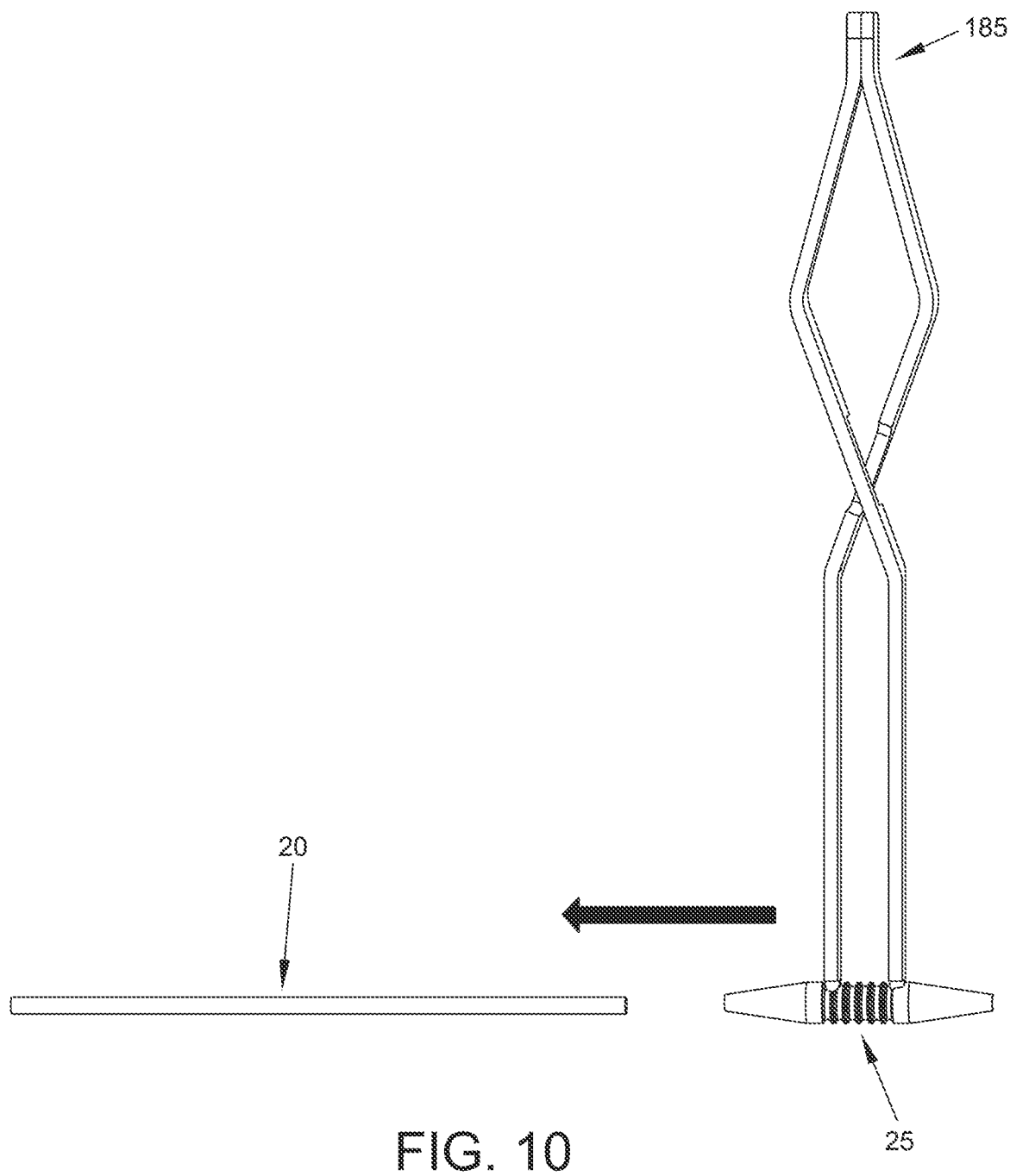
FIGS. 10-12 are schematic views showing use of the novel catheter line fixation device of FIGS. 3-6.
Figure 11:
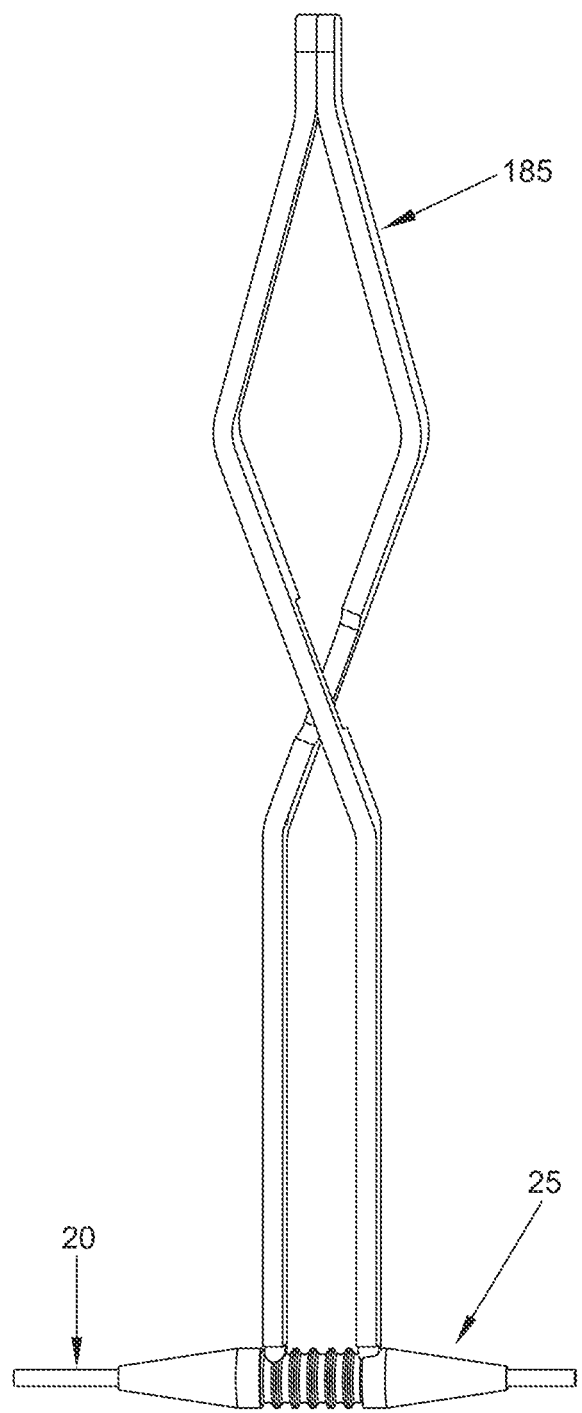
Figure 12:
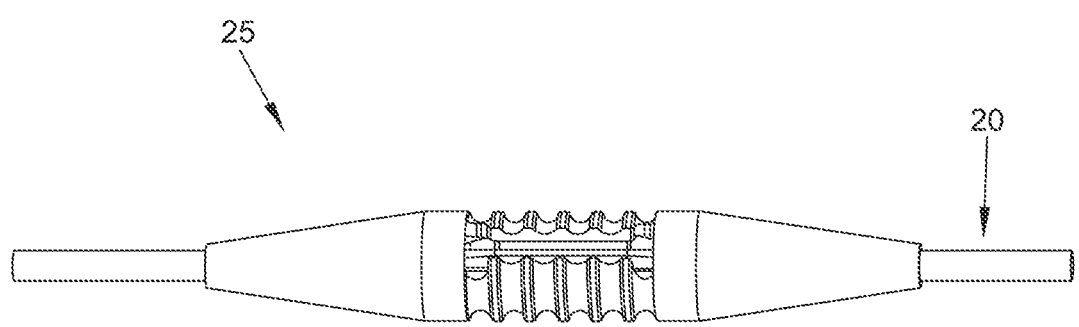

More particularly, and looking now at FIGS. 10-12, when a catheter line fixation device 25 is to loaded onto catheter line 20, a tool 185 is used to longitudinally expand (i.e., open) catheter line fixation device 25. More particularly, tool 185 is inserted into opening 100 of intermediate portion 60 of housing 30 and used to move distal end portion 40 of housing 30 and proximal end portion 45 of housing 30 away from one another. This longitudinal expansion (i.e., stretching) of housing 30 moves tapered distal collet collar 110 off of tapered distal end region 130 of body 105 and moves hourglass-shaped proximal collet collar 115 off of tapered proximal end region 140 of body 105, thereby allowing body 105 of collet assembly 35 to expand (i.e., open) on hinges 180. Once body 105 of collet assembly 35 is expanded, catheter line fixation device 25 is loaded onto catheter line 20 by passing a free end of catheter line 20 through passageway 70 of housing 30 (and through bore 155 of body 105 of collet assembly 35). Note that the expanded catheter line fixation device 25 is able to move easily over catheter line 20 due to the sizing of distal end section 75 of passageway 70, and due to the sizing of proximal end section 80 of passageway 70, relative to the outer diameter of catheter line 20, and due to the expanded size of bore 155 of body 105 of collet assembly 35 relative to the outer diameter of catheter line 20.

Catheter line fixation device 25 is then moved along catheter line 20 until catheter line fixation device 25 is disposed at the desired location for fixation.

When catheter line fixation device 25 is to be secured to catheter line 20, tool 185 is removed from opening 100 of intermediate section 85 of passageway 70. The removal of tool 185 from opening 100 allows catheter line fixation device 25 to contract longitudinally (i.e., to shorten longitudinally) and thereby "clamp" on to catheter line 20. More particularly, as catheter line fixation device 25 contracts longitudinally, distal collet collar 110 moves back over tapered distal end region 130 of body 105 of collet assembly 35, and hourglass-shaped proximal collet collar 115 moves back over tapered proximal end region 140 of body 105 of collet assembly 35, thereby compressing body 105 about hinges 180 so that collet assembly 35 "clamps" onto catheter line 20.

With catheter line fixation device 25 secured at the desired location along catheter line 20, sutures are used to secure catheter line fixation device 25 to the tissue of the patient (e.g., the internal fascia of the patient), with the sutures seating in the troughs 66 disposed between ribs 65 of intermediate portion 60 of housing 30, whereby to secure catheter line fixation device 25 to the patient.

Note that, if desired, distal collet collar 110 and hourglass-shaped proximal collet collar 115 may terminate in alignment with the distal and proximal ends of opening 100 of housing 30, respectively, and tool 185 may be configured to directly engage the proximal-most end of distal collet collar 110 and to directly engage the distal-most end of hourglass-shaped proximal collet collar 115 (as well as to directly engage housing 30), such that tool 185 can directly force apart distal collet collar 110 and hourglass-shaped proximal collet collar 115.

If desired, ribs 65 of intermediate portion 60 of housing 30 may be supplemented by, or replaced by, suture eyelets.

Figure 13:
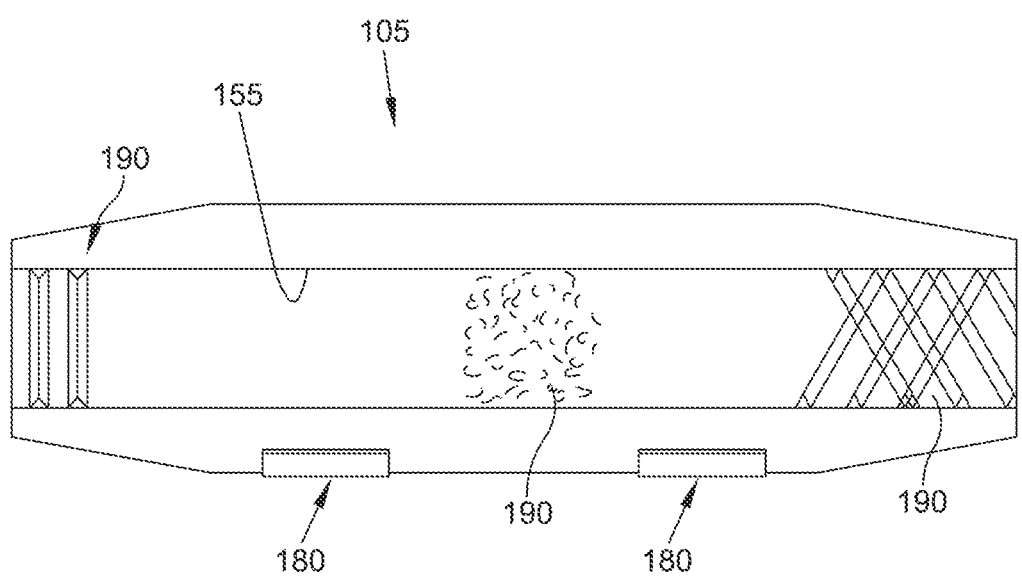
FIG. 13 is a schematic view showing an alternative form of the body of the collet assembly.
Figure 14:
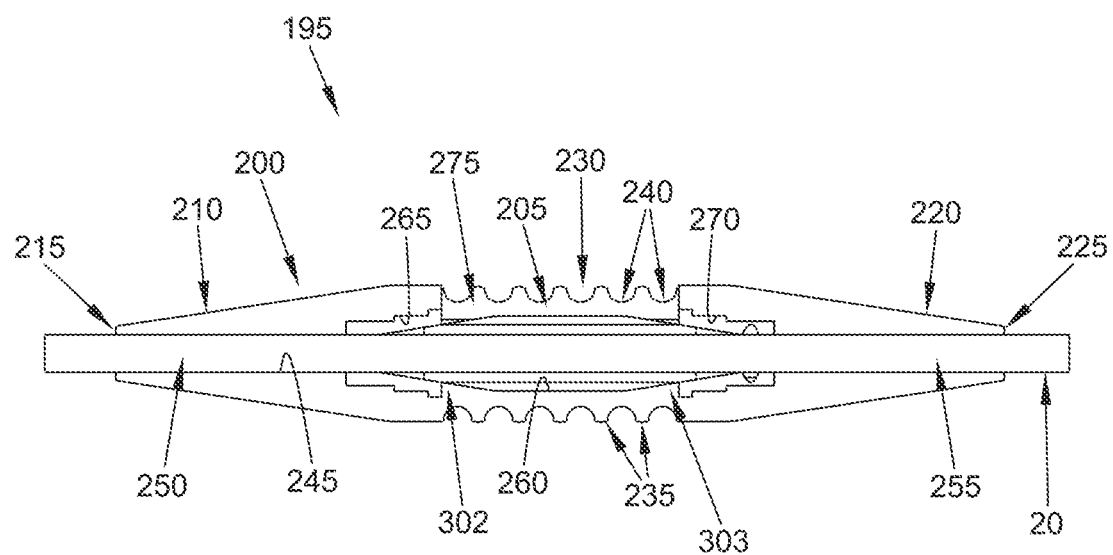
FIGS. 14-18 are schematic views showing another novel catheter line fixation device formed in accordance with the present invention.
Figure 15:
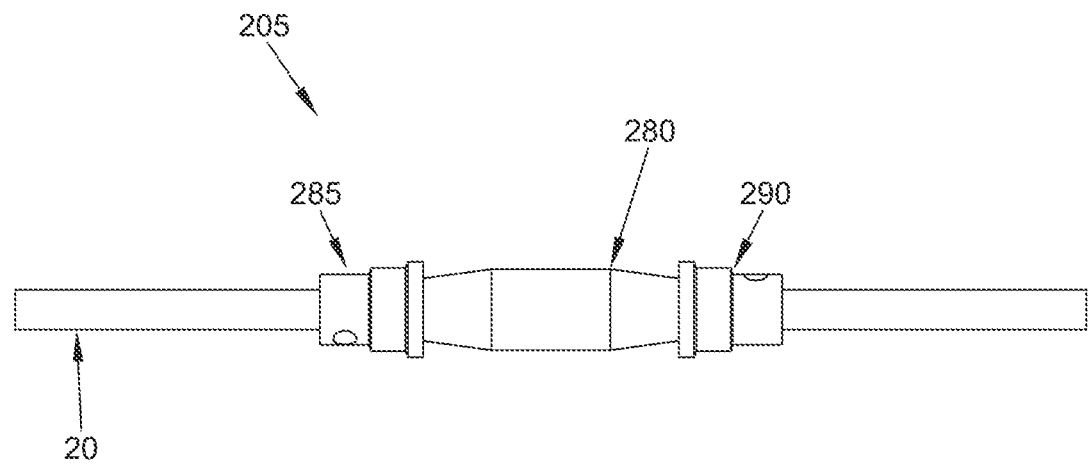
Figure 16:
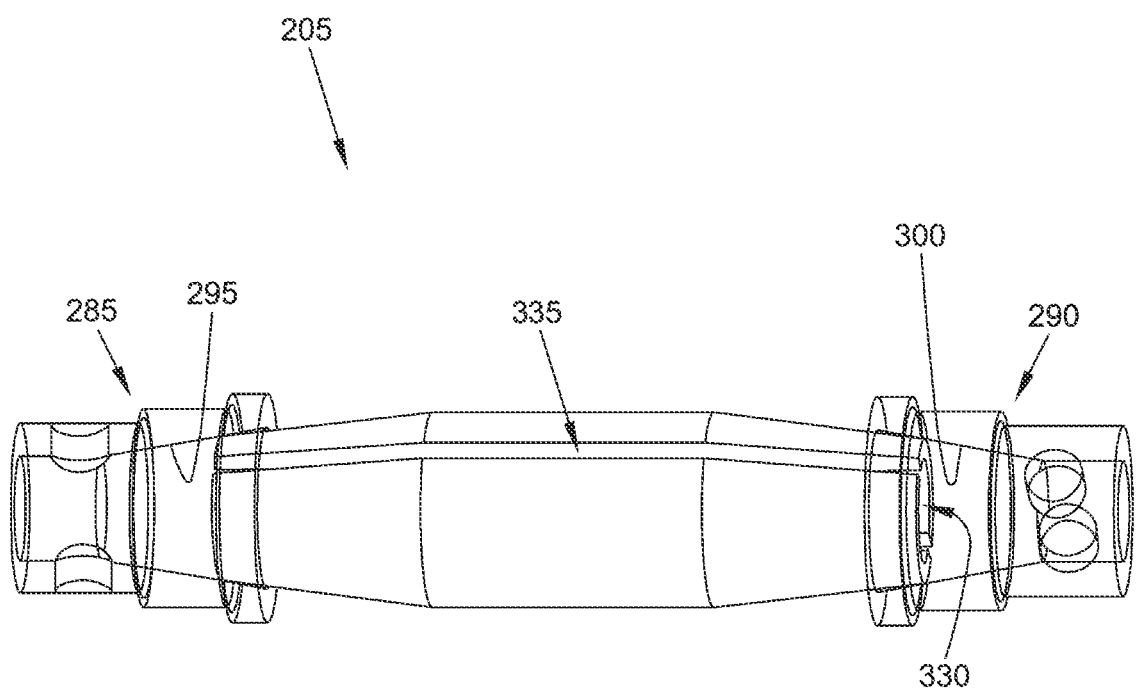
Figure 17:
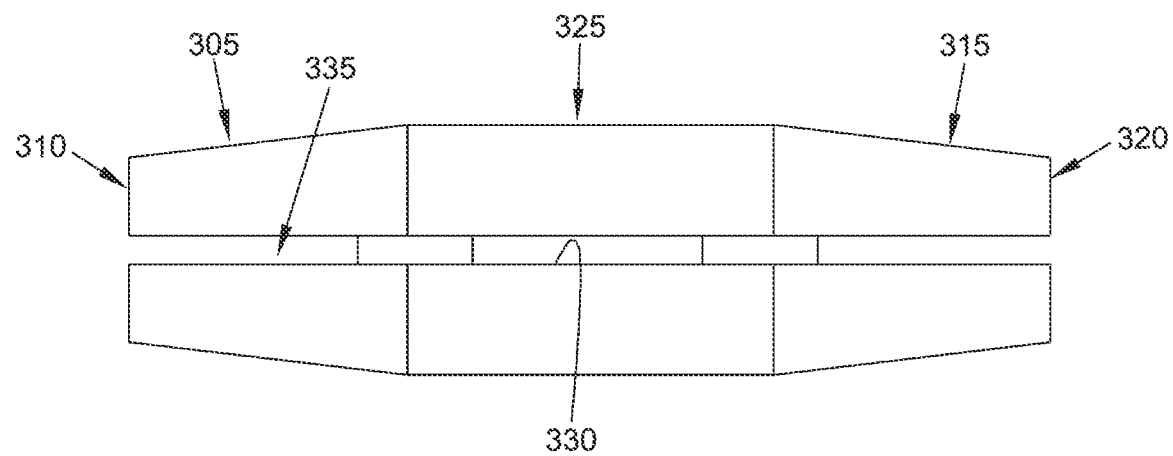
Figure 18:
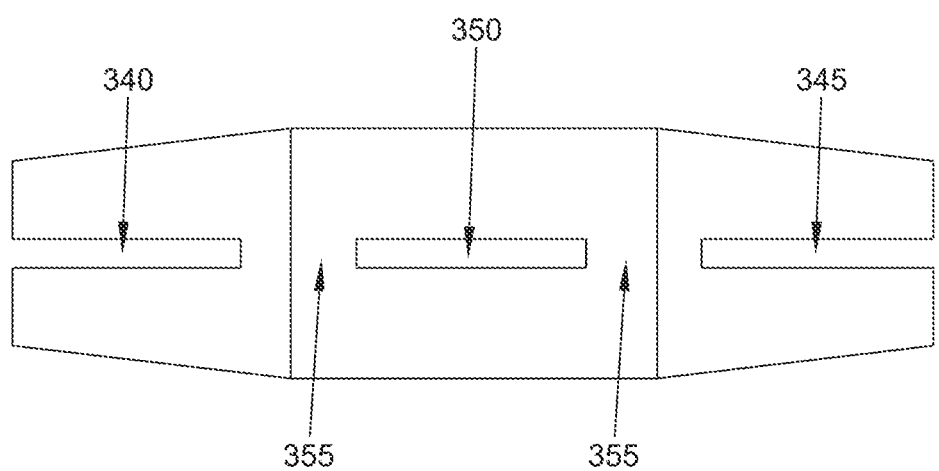

Also, if desired, and looking now at FIG. 13, the side wall of bore 155 of body 105 may comprise surface features 190 (e.g., rings, grooves, ribs, cross-hatching, surface texturing, etc.) so as to enhance gripping of catheter line 20 when body 150 clamps down on a catheter line. Such surface features may extend the entire length of bore 155 or may be disposed at selected regions of bore 155. See, for example, the ribs, surface texturing and cross-hatch grooves disposed along bore 155 in FIG. 13.

In the foregoing description, distal collet collar 110 and proximal collet collar 115 are disclosed as having different shapes, e.g., distal collet collar 110 is disclosed as tapered (e.g., frustoconical) and proximal collet collar 115 is disclosed as hourglass-shaped. However, distal collet collar 110 and proximal collet collar 115 may have the same shape, e.g., they may both be tapered (e.g., frustoconical), or they may both be hourglass-shaped, etc. Of course, to the extent that distal collet collar 110 and proximal collet collar 115 have shapes other than those disclosed above, sections 90 and 95 of passageway 70 will have complementary shapes to distal collet collar 110 and proximal collet collar 115, respectively.

In connection with the foregoing, it will be appreciated that multiple catheter lines may be required to appropriately treat the patient, so multiple catheter line fixation devices 25 may be used, i.e., one catheter line fixation device 25 for each of the catheter lines. And it should also be appreciated that, if desired, more than one catheter fixation device 25 may be used for each catheter line, e.g., such as for situations where increased "holding power" is desired or where the catheter line must be stabilized at multiple locations.

Alternative Catheter Fixation Device with Stepped Collet Collars and Correspondingly Stepped Passageway in the Housing If desired, the catheter line fixation device 25 discussed above may be modified so as to better facilitate longitudinal movement of collet collars 110, 115 during longitudinal stretching (and longitudinal contraction) of housing 30.

More particularly, and looking now at FIGS. 14-18, there is shown another novel catheter line fixation device 195 formed in accordance with the present invention. Catheter line fixation device 195 is generally similar to the catheter line fixation device 25 discussed above, however, in this form of the invention, the housing and the collet assembly are modified in order to enhance longitudinal movement of the collet collars during longitudinal stretching (and longitudinal contraction) of the housing, whereby to facilitate more efficient release from (and engagement with) the collet collars of the body of the collet assembly, as will hereinafter be discussed in further detail.

More particularly, catheter line fixation device 195 generally comprises a housing 200 and a collet assembly 205. As will hereinafter be discussed, collet assembly 205 is disposed within housing 200 and serves to adjustably secure housing 200 of catheter line fixation device 195 to catheter line 20.

Housing 200 generally comprises a distal end portion 210 terminating in a distal end surface 215, a proximal end portion 220 terminating in a proximal end surface 225, and an intermediate portion 230 disposed between distal end portion 210 and proximal end portion 220.

In one preferred form of the invention, distal end portion 210 and proximal end portion 220 are tapered.

And in one preferred form of the invention, intermediate portion 230 comprises ribs 235 for receiving suture for securing catheter line fixation device 195 to the tissue of a patient (e.g., the internal fascia of a patient). More particularly, the troughs 240 disposed between the ribs 235 serve as seats for receiving the suture which secures catheter line fixation device 195 to the tissue of a patient. Preferably the entire housing 200 is formed out of elastomeric material. Alternatively, intermediate portion 230 of housing 200 is formed out of elastomeric material and distal end portion 210 of housing 200, and proximal end portion 220 of housing 200, are formed out of non-elastomeric material(s).

A passageway 245 extends between distal end surface 215 and proximal end surface 225. More particularly, passageway 245 comprises a distal end section 250, a proximal end section 255 and an intermediate section 260. Passageway 245 also comprises a distal stepped section 265 which is located between distal end section 250 and intermediate section 260, and a proximal stepped section 270 which is located between proximal end section 255 and intermediate section 260. Thus, proceeding distal to proximal, passageway 245 comprises the aforementioned distal end section 250, distal stepped section 265, intermediate section 230, proximal stepped section 270 and proximal end section 255. Distal end section 250 and proximal end section 255 are both sized so as to be just slightly larger than the outer diameter of catheter line 20, such that catheter line 20 can slide through distal end section 250 and proximal end section 255 (see below).

In a preferred form of the invention, distal stepped section 265 comprises a stepped "taper" (e.g., a plurality of counterbores having decreasing diameters moving distally away from intermediate section 260 of passageway 245) for receiving a stepped distal collet collar (see below), and proximal stepped section 270 comprises a stepped "taper" (e.g., a plurality of counterbores having decreasing diameters moving proximally away from intermediate section 260 of passageway 245) for receiving a stepped proximal collet collar, as will hereinafter be discussed in further detail.

In a preferred form of the invention, an opening 275 is formed in intermediate section 260 of passageway 245. Opening 275 communicates with intermediate section 260 of passageway 245 and preferably also communicates with the proximal-most portion of distal stepped section 265 and the distal-most portion of proximal stepped section 270 so as to permit an insertion tool to be used to contact a distal collet collar (see below) disposed in distal stepped section 265 of passageway 245 and a proximal collet collar (see below) disposed in proximal stepped section 270, as will hereinafter be discussed.

Collet assembly 205 generally comprises a body 280, a stepped distal collet collar 285 and a stepped proximal collet collar 290. Stepped distal collet collar 285 comprises a tapered opening 295, and stepped proximal collet collar 290 comprises a tapered opening 300. Stepped distal collet collar 285 is sized so as to be received within, and be secured to, distal stepped section 265 of passageway 245, and stepped proximal collet collar 290 is sized so as to be received within, and be secured to, proximal stepped section 270 of passageway 245. In this respect, it should be appreciated that the "steps" of stepped distal collet collar 285 and proximal collet collar 290 engage the corresponding "steps" formed in distal stepped section 265 and proximal stepped section 270, respectively, whereby to act as bearing surfaces for transmitting forces between (i) stepped distal collet collar 285 and housing 200, and (ii) stepped proximal collet collar 290 and housing 200.

Note that, if desired, a portion 302 of housing 200 may be disposed proximal to, and radially inward of, the proximal-most portion of stepped distal collet collar 285, and a portion 303 of housing 200 may be disposed distal to, and radially inward of, the distal-most portion of stepped proximal collet collar 290, such that when housing 200 is stretched apart, stepped distal collet collar 285 and stepped proximal collet collar 290 will also be stretched apart.

In one form of the invention, stepped distal collet collar 285 is molded into distal stepped section 265 of passageway 245, and stepped proximal collet collar 290 is molded into proximal stepped section 270 of passageway 245. Note that stepped distal collet collar 285 and/or stepped proximal collet collar 290 may be formed out of a material which is harder and/or less elastic than the material out of which housing 200 is formed.

Body 280 of collet assembly 205 comprises a tapered distal end region 305 terminating in a distal end surface 310, a tapered proximal end region 315 terminating in a proximal end surface 320, and a tubular intermediate region 325 extending between tapered distal end region 305 and tapered proximal end region 315. Tapered distal end region 305 of body 280 is slidably received within tapered opening 295 of stepped distal collet collar 285, and tapered proximal end region 315 of body 280 is slidably received within tapered opening 300 of stepped proximal collet collar 290. A bore 330 extends through body 280, from distal end surface 310 to proximal end surface 320. Bore 330 is sized so as to be slightly smaller than the outer diameter of catheter line 20 when body 280 is in an unbiased condition (see below).

A slot 335 is formed in tapered distal end region 305, tubular intermediate region 325 and tapered proximal end region 315. Slot 335 communicates with bore 330.

A distal opening 340 is formed in tapered distal end region 305 and tubular intermediate region 325, a proximal opening 345 is formed in tapered proximal end region 315 and tubular intermediate region 325, and an intermediate opening 350 is formed in tubular intermediate region 325. Distal opening 340, intermediate opening 350 and proximal opening 345 are aligned with one another, and are diametrically opposed from slot 335. Distal opening 340, intermediate opening 350 and proximal opening 345 together define a pair of hinges 355.

At least hinges 355, and preferably the entire body 280 of collet assembly 205, comprise an elastomeric material, such that body 280 of collet assembly 205 can open and close about slot 335 on flexible hinges 355.

Collet assembly 205 is mounted within housing 200 so that (i) stepped distal collet collar 285 of collet assembly 205 is received within, and is secured to, distal stepped section 265 of passageway 245, (ii) stepped proximal collet collar 290 of collet assembly 205 is received within, and is secured to, proximal stepped section 270 of passageway 245, and (iii) body 280 of collet assembly 205 is disposed within intermediate section 260 of passageway 245.

As a result of this construction, when distal end portion 210 of housing 200 and proximal end portion 220 of housing 200 are forced apart, stepped distal collet collar 285 of collet assembly 205 and stepped proximal collet collar 290 of collet assembly 205 are also forced apart (i.e., by virtue of the fact that stepped distal collet collar 285 is received within, and is secured to, distal stepped section 265 of passageway 245, and by virtue of the fact that stepped proximal collet collar 290 is received within, and is secured to, proximal stepped section 270 of passageway 245), whereby to move stepped distal collet collar 285 away from tapered distal end region 305 of body 280 and whereby to move stepped proximal collet collar 290 away from tapered proximal end region 315 of body 280, so as to allow body 280 of collet assembly 205 to assume an unbiased condition and open on its hinges 355. In other words, when the two ends of housing 200 are stretched longitudinally apart, body 280 of collet assembly 205 is radially uncompressed.

Conversely, when the stretching force applied to distal end portion 210 of housing 200 and proximal end portion 220 of housing 200 is relaxed, and distal end portion 210 of housing 200 and proximal end portion 220 of housing 200 are allowed to return back towards one another (i.e., due to the elastomeric nature of intermediate portion 230 of housing 200), stepped distal collet collar 285 of collet assembly 205 and stepped proximal collet collar 290 of collet assembly 205 also return back towards one another (i.e., by virtue of the fact that stepped distal collet collar 285 is received within, and is secured to, distal stepped section 265 of passageway 245, and by virtue of the fact that stepped proximal collet collar 290 is received within, and is secured to, proximal stepped section 270 of passageway 245), whereby to force stepped distal collet collar 285 against tapered distal end region 305 of body 280 and whereby to force stepped proximal collet collar 290 against tapered proximal end region 315 of body 280, so as to cause body 280 of collet assembly 205 to assume a biased condition and close on its hinges 355. In other words, when the two ends of housing 200 are no longer stretched longitudinally apart, body 280 of collet assembly 205 is radially compressed.

Note that inasmuch as housing 200 (or at least intermediate portion 230 of housing 200) is elastomeric, stepped distal collet collar 285 of collet assembly 205 and stepped proximal collet collar 290 of collet assembly 205 are normally biased together, whereby to close body 280 of collet assembly 205 on its hinges 355. Note also that when body 280 of collet assembly 205 is closed on its hinges 355, bore 330 of body 280 has a diameter smaller than the outer diameter of catheter line 20.

Thus, when distal end portion 210 of housing 200 and proximal end portion 220 of housing 200 are forced apart, body 280 of collet assembly 205 is able to open on its hinges, such that a catheter line 20 can be passed through bore 330 of body 280 and hence through passageway 245 of housing 200.

Conversely, when the stretching force applied to distal end portion 210 of housing 200 and proximal end portion 220 of housing 200 is thereafter released, body 280 of collet assembly 205 closes back down on its hinges 355, such that body 280 of collet assembly 205 securely grips a catheter line 20 which has been previously passed through bore 330 of body 280 and passageway 245 of housing 200.

Alternative Tools for Longitudinally Expanding Catheter Fixation Devices 25, 195

As discussed above, in one form of the invention, a tool 185 (FIGS. 10-12) may be used to longitudinally expand (i.e., open) catheter line fixation device 25 by inserting tool 185 into opening 100 of intermediate portion 60 of housing 30 and using tool 185 to move distal end portion 40 of housing 30 and proximal end portion 50 of housing 30 away from one another. It should be appreciated that the aforementioned tool 185 may also be used to longitudinally expand (i.e., open) catheter line fixation device 195 in the same manner (i.e., by inserting tool 185 into opening 275 of intermediate portion 230 of housing 200 and using tool 185 to move distal end portion 210 of housing 200 and proximal end portion 220 of housing 200 away from one another).

However, if desired, it may be desirable to provide a novel tool that can be passed into opening 100 of intermediate portion 60 of housing 30 (or into opening 275 of intermediate portion 230 of housing 200) such that the tool directly engages tapered distal collet collar 110 and hourglass-shaped proximal collet collar 115 (or stepped distal collet collar 285 and stepped proximal collet collar 290) so as to transmit the stretching force to the collet collars 110, 115 (or collet collars 285, 290) as well as to the housing 30 (or housing 200).

Figure 19:
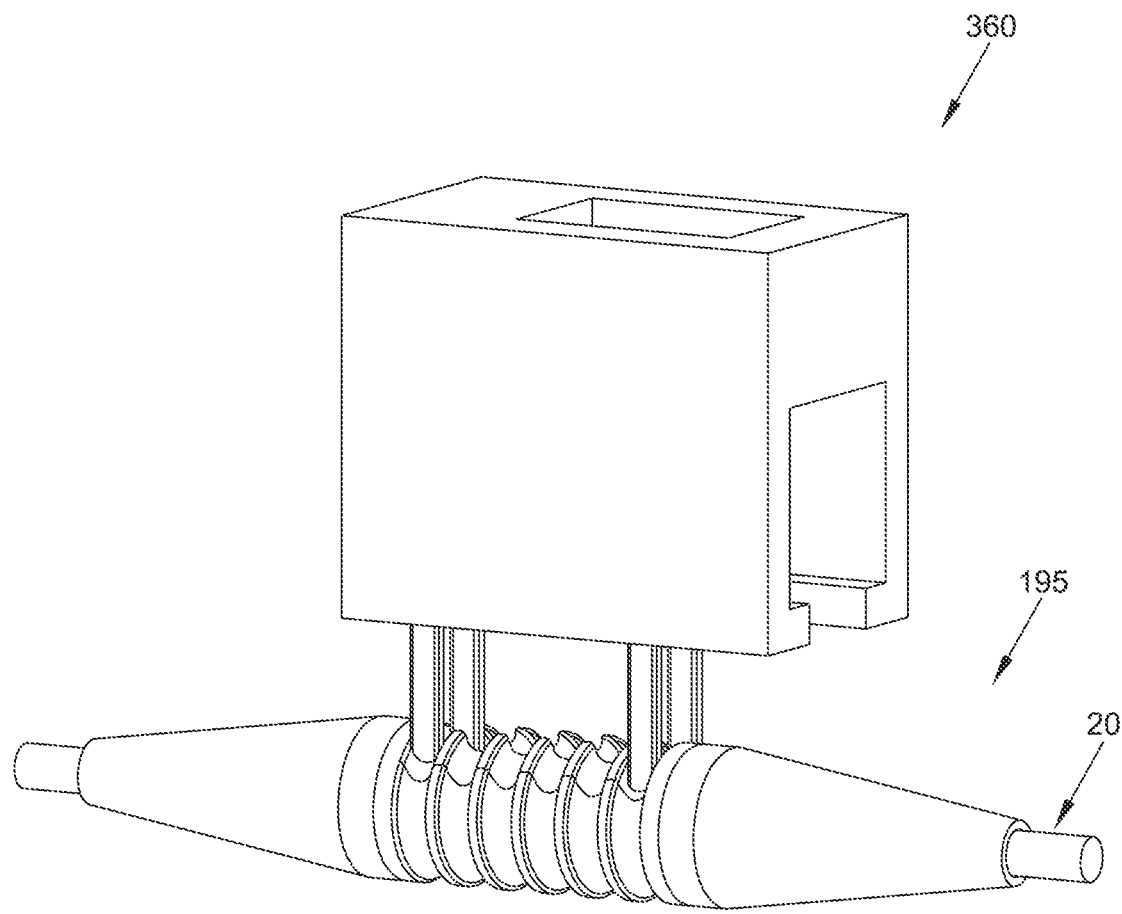
FIGS. 19 and 20 are schematic views showing another tool which may be used to deploy a novel catheter line fixation device formed in accordance with the present invention.
Figure 20:
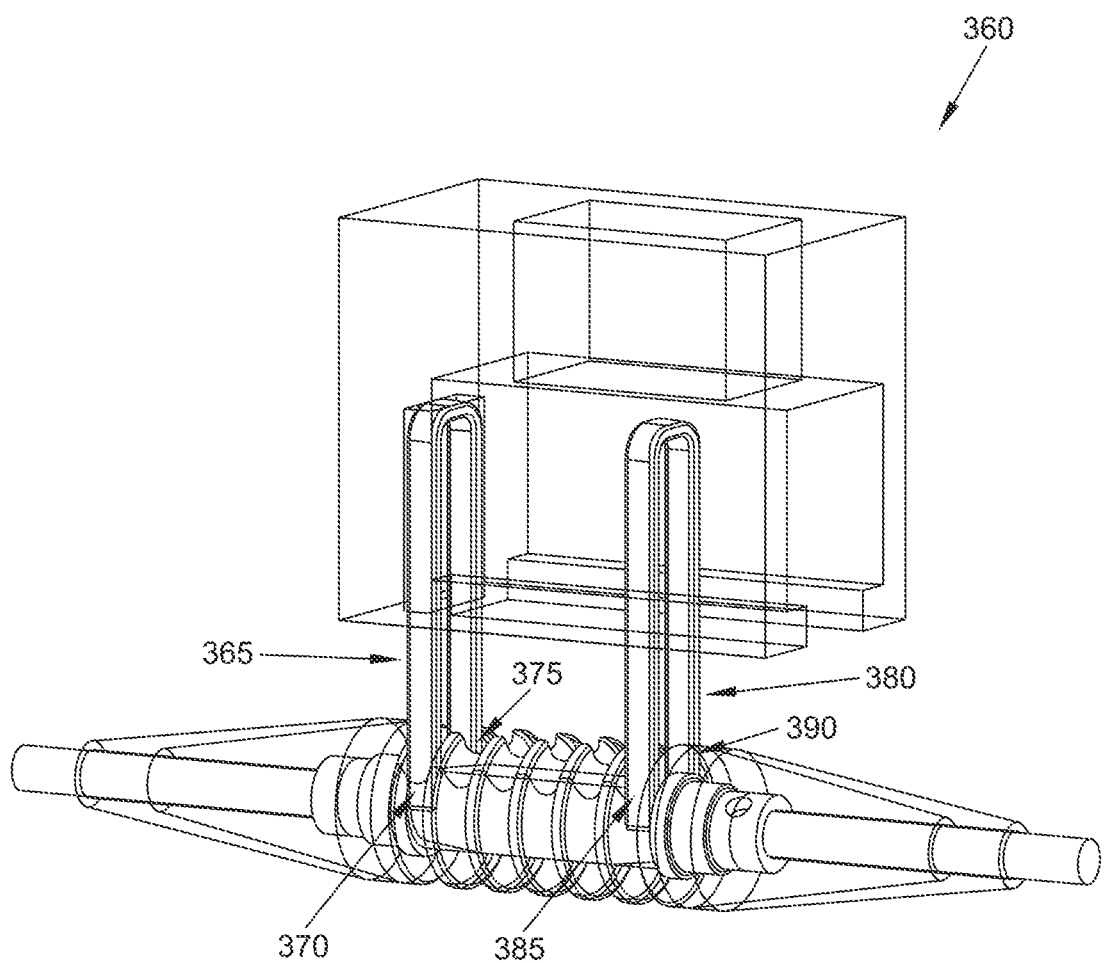

To that end, and looking now at FIGS. 19 and 20, there is shown a novel tool 360 formed in accordance with the present invention. Tool 360 comprises a distal tine 365 having a pair of free ends 370, 375 sized to be received in opening 100 of intermediate portion 60 of housing 30 (or in opening 275 of intermediate portion 230 of housing 200), and a proximal tine 380 having a pair of free ends 385, 390 sized to be received in opening 100 of intermediate portion 60 of housing 30 (or in opening 275 of intermediate portion 230 of housing 200).

Free ends 370, 375 of distal tine 365 and free ends 385, 390 of proximal tine 380 are separated from one another by a gap that is slightly larger than the diameter of body 105 of collet assembly 35 (or body 280 of collet assembly 205) when body 105 (or body 280) is in its unbiased, radially-expanded condition.

Free ends 370, 375 of distal tine 365 contact the proximally-facing end of tapered distal collet collar 110 (or the proximally-facing end of stepped distal collet collar 285) and housing 30 (or housing 200), and free ends 385, 390 of proximal tine 380 contact the distally-facing end of hourglass-shaped proximal collet collar 115 (or the distally-facing end of stepped proximal collet collar 290) and housing 30 (or housing 200) when distal tine 365 and proximal tine 380 of tool 360 are inserted into opening 100 of intermediate portion 60 of housing 30.

Distal tine 365 and proximal tine 380 are then moved apart from one another (e.g., by a mechanism, not shown, but which will be apparent to one skilled in the art in view of the present disclosure), which moves one of the tines 365, 380 relative to the other of the tines (or which moves both tines 365, 380 in opposite directions). As this occurs, free ends 370, 375 of distal tine 365 and free ends 385, 390 of proximal tine 380 bear against the proximally-facing surface of tapered distal collet collar 110 (or the proximally-facing surface of stepped distal collet collar 285) and housing 30 (or housing 200), and free ends 385, 390 of proximal tine 380 bear against the distally-facing surface of hourglass-shaped proximal collet collar 115 (or the distally-facing surface of stepped proximal collet collar 390) and housing 30 (or housing 200), whereby to "push" tapered distal collet collar 110 (or stepped distal collet collar 285) and distal end portion 40 of housing 30 (or distal end portion 210 of housing 200) distally, and whereby to "push" hourglass-shaped proximal collet collar 115 (or stepped proximal collet collar 290) and proximal end portion 50 of housing 30 (or proximal end portion 220 of housing 200) proximally.

As a result, housing 30 (or housing 200) is stretched longitudinally, and distal collet collar 110 (or stepped distal collet collar 285) and hourglass-shaped proximal collet collar 115 (or stepped proximal collet collar 290) are moved apart, whereby to release collet body 105 (or collet body 280) from constraint so as to allow collet body 105 (or collet body 280) to assume its unbiased, radially-expanded condition.

When this happens, the diameter of bore 155 of body 105 (or the diameter of bore 330 of body 280) is slightly larger than the diameter of catheter line 20, and catheter line fixation device 25 (or catheter line fixation device 195) may be slid along catheter line 20 until it is in the desired position relative to the patient's anatomy/desired position along catheter line 20.

When catheter line fixation device 25 (or catheter line fixation device 195) is in the desired position, distal tine 365 and proximal tine 380 are moved toward one another, releasing the outwardly-directed force on tapered distal collet collar 110 (or stepped distal collet collar 285) and housing 30 (or housing 200), and releasing the outwardly-directed force on hourglass-shaped proximal collet collar 115 (or stepped proximal collet collar 290) and housing 30 (or housing 200), whereby to permit housing 30 (or housing 200) to longitudinally contract (i.e., due to the elastomeric nature of housing 30, 200), whereby to induce collet body 105 (or collet body 280) into assuming its biased, radially-contracted condition (see above). When this occurs, bore 155 (or bore 330) of body 105 (or body 280) radially contracts such that bore 155 (or bore 330) is slightly smaller than catheter line 20, whereby to secure collet body 105 (or collet body 280) to catheter line 20, and hence to secure catheter line fixation device 25 (or catheter line fixation device 195) to catheter line 20.

Tool 360 is then removed and the catheter line fixation device may be secured to the anatomy (e.g., using sutures in the manner discussed above).

Alternative Collet Body

In addition to the foregoing, it should also be appreciated that, if desired, body 105 of collet assembly 35 (or body 280 of collet assembly 205) may be formed as two separate halves, omitting hinges 180 (or hinges 355).

Figure 21:
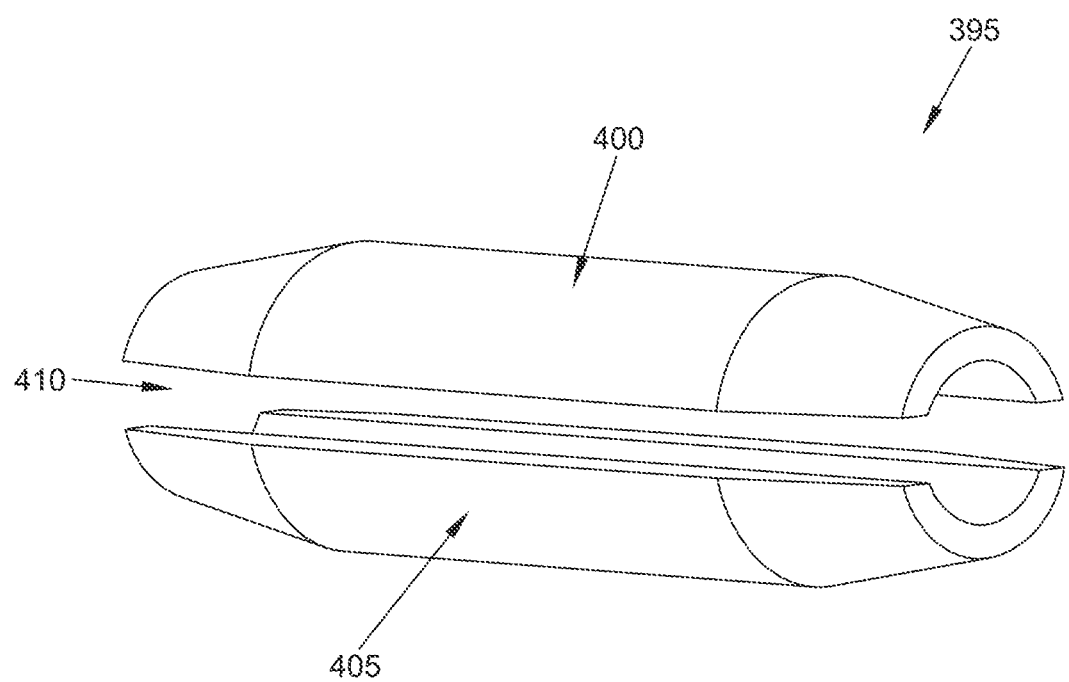
FIG. 21 is a schematic view showing an alternative form of the body of the collet assembly.

By way of example but not limitation, and looking now at FIG. 21, there is shown an alternative collet body 395 formed in accordance with the present invention. Collet body 395 is shaped generally similar to the aforementioned collet bodies 105, 280, however, in this form of the invention, collet body 395 comprises two halves 400, 405. When collet body 395 is in its unbiased, radially-expanded condition, halves 400, 405 are separated by a gap 410 such that collet body 395 is able to slide freely relative to a catheter line 20 disposed between halves 400, 405. When collet body 395 is in its biased, radially-compressed condition, halves 400, 405 move toward one another and "close up" gap 410, whereby to compress a catheter line 20 disposed in gap 410 and hence "clamp" catheter line 20 to collet body 395, thereby securing catheter line fixation device 25 (or catheter line fixation device 195) to catheter line 20.

Use of the Present Invention for Other Applications

It should be appreciated that the present invention may be used for applications other than anchoring catheter lines to a patient for pain pump drug delivery. By way of example but not limitation, the present invention may also be used to secure electrical leads, intravenous (IV) lines, and/or substantially any other elongated, flexible element to a patient.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An apparatus for releasably securing an elongated component to tissue, said apparatus comprising:
    a housing comprising:
        a distal end portion terminating in a distal end surface, a proximal end portion terminating in a proximal end surface, and an intermediate portion disposed between said distal end portion and said proximal end portion; and
        a passageway extending through said housing from said distal end surface to said proximal end surface, said passageway comprising a distal end section, a proximal end section, and an intermediate section disposed between said distal end section and said proximal end section;
        wherein at least a portion of said housing is formed out of an elastomeric material so that said housing may be selectively longitudinally stretched so as to transform from a longitudinally-relaxed condition to a longitudinally-stretched condition; and
    a collet assembly for disposition in said passageway of said housing, said collet assembly comprising:
        a radially-compressible body comprising a tapered distal end region terminating in a distal end surface, a tapered proximal end region terminating in a proximal end surface, and a tubular intermediate region disposed between said tapered distal end region and said tapered proximal end region; and
        a bore extending between said distal end surface of said body and said proximal end surface of said body, said bore being sized larger than the elongated component when said body is in a radially-uncompressed condition;
    wherein said tapered distal end region of said body of said collet assembly is received in said distal end section of said passageway of said housing, and said tapered proximal end region of said body of said collet assembly is received in said proximal end section of said passageway of said housing;
    wherein, when said housing is in the longitudinally-relaxed condition, said distal end section of said passageway of said housing engages said tapered distal end region of said body of said collet assembly, and said proximal end section of said passageway of said housing engages said tapered proximal end region of said body of said collet assembly, so as to radially compress said body of said collet assembly into a radially-compressed condition wherein said bore is sized smaller than the elongated component; and
    wherein, when said housing is in the longitudinally-stretched condition, said distal end section of said passageway of said housing disengages from said tapered distal end region of said body of said collet assembly, and said proximal end section of said passageway of said housing disengages from said tapered proximal end region of said body of said collet assembly, so as to no longer radially compress said body of said collet assembly.

2. The apparatus according to claim 1 wherein said tapered distal end region of said body of said collet assembly tapers inwardly in a distal direction, and said tapered proximal end region of said body of said collet assembly tapers inwardly in a proximal direction.

3. The apparatus according to claim 1 further comprising a distal collet collar for engaging said tapered distal end region of said body of said collet assembly, and a proximal collet collar for engaging said tapered proximal end region of said body of said collet assembly.

4. The apparatus according to claim 3 wherein said distal collet collar comprises an internal opening which tapers inwardly in a distal direction.

5. The apparatus according to claim 3 wherein said proximal collet collar comprises an internal opening which tapers inwardly in a proximal direction.

6. The apparatus according to claim 1 wherein said body of said collet assembly comprises a first slot opening on said bore, said first slot extending from said distal end surface of said body to said proximal end surface of said body.

7. The apparatus according to claim 6 wherein said collet assembly further comprises at least one second slot opening on said bore, said at least one second slot being diametrically-opposed to said first slot.

8. The apparatus according to claim 7 wherein said at least one second slot comprises a plurality of second slots, and further wherein each of said second slots is separated from others of said second slots by a flexible portion of said body of said collet assembly.

9. The apparatus according to claim 1 wherein said intermediate portion of said housing comprises at least one opening extending radially inwardly towards said passageway of said housing.

10. The apparatus according to claim 9 wherein said at least one opening communicates with said passageway of said housing.

11. The apparatus according to claim 1 wherein said intermediate portion comprises a plurality of ribs.

12. The apparatus according to claim 1 wherein said distal end portion of said housing tapers inwardly in a distal direction and said proximal end portion of said housing tapers inwardly in a proximal direction.

13. The apparatus according to claim 1 wherein the elongated component is one selected from the group consisting of: a catheter and an electrical lead.

14. The apparatus according to claim 1 wherein said intermediate portion of said housing is elastomeric.

15. The apparatus according to claim 1 wherein the entire housing is elastomeric.

16. A method for securing an elongated component to tissue, said method comprising:
    providing an apparatus for releasably securing the elongated component to the tissue, said apparatus comprising:
        a housing comprising:
            a distal end portion terminating in a distal end surface, a proximal end portion terminating in a proximal end surface, and an intermediate portion disposed between said distal end portion and said proximal end portion; and
            a passageway extending through said housing from said distal end surface to said proximal end surface, said passageway comprising a distal end section, a proximal end section, and an intermediate section disposed between said distal end section and said proximal end section;

wherein at least a portion of said housing is formed out of an elastomeric material so that said housing may be selectively longitudinally stretched so as to transform from a longitudinally-relaxed condition to a longitudinally-stretched condition; and a collet assembly for disposition in said passageway of said housing, said collet assembly comprising:

a radially-compressible body comprising a tapered distal end region terminating in a distal end surface, a tapered proximal end region terminating in a proximal end surface, and a tubular intermediate region disposed between said tapered distal end region and said tapered proximal end region; and a bore extending between said distal end surface of said body and said proximal end surface of said body, said bore being sized larger than the elongated component when said body is in a radially-uncompressed condition;

wherein said tapered distal end region of said body of said collet assembly is received in said distal end section of said passageway of said housing, and said tapered proximal end region of said body of said collet assembly is received in said proximal end section of said passageway of said housing;

wherein, when said housing is in the longitudinally-relaxed condition, said distal end section of said passageway of said housing engages said tapered distal end region of said body of said collet assembly, and said proximal end section of said passageway of said housing engages said tapered proximal end region of said body of said collet assembly, so as to radially compress said body of said collet assembly into a radially-compressed condition wherein said bore is sized smaller than the elongated component; and wherein, when said housing is in the longitudinally-stretched condition, said distal end section of said passageway of said housing disengages from said tapered distal end region of said body of said collet assembly, and said proximal end section of said passageway of said housing disengages from said tapered proximal end region of said body of said collet assembly, so as to no longer radially compress said body of said collet assembly;

applying a longitudinally-stretching force to said housing so as to transform said housing from the longitudinally-relaxed condition to the longitudinally-stretched condition, whereby to transform said body of said collet assembly from the radially-compressed condition to the radially-uncompressed condition;

passing the elongated component through said passageway of said housing and said bore of said collet assembly;

removing the longitudinally-stretching force from said housing so as to transform said housing from the longitudinally-stretched condition to the longitudinally-relaxed condition, whereby to transform said body of said collet assembly from the radially-uncompressed condition to the radially-compressed condition; and securing said housing to the tissue.

17. The method according to claim 16 wherein securing said housing to the tissue comprises suturing said housing to the tissue.

18. The method according to claim 17 wherein said intermediate portion of said housing comprises a plurality of ribs, and further wherein the suturing said housing to the tissue comprises passing a suture between said plurality of ribs.

* * * * *